(12) United States Patent
Galipeau et al.

(10) Patent No.: US 11,701,389 B2
(45) Date of Patent: Jul. 18, 2023

(54) METHODS OF PRESERVING MESENCHYMAL STEM CELLS

(71) Applicants: Emory University, Atlanta, GA (US); Children's Healthcare of Atlanta, Inc., Atlanta, GA (US)

(72) Inventors: Jacques Galipeau, Madison, WI (US); Raghavan Chinnadurai, Tucker, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 516 days.

(21) Appl. No.: 16/083,661

(22) PCT Filed: Mar. 9, 2017

(86) PCT No.: PCT/US2017/021523
§ 371 (c)(1),
(2) Date: Sep. 10, 2018

(87) PCT Pub. No.: WO2017/156235
PCT Pub. Date: Sep. 14, 2017

(65) Prior Publication Data
US 2019/0099449 A1 Apr. 4, 2019

Related U.S. Application Data

(60) Provisional application No. 62/305,644, filed on Mar. 9, 2016.

(51) Int. Cl.
*A61K 35/28* (2015.01)
*A01N 1/02* (2006.01)
*C12N 5/0775* (2010.01)

(52) U.S. Cl.
CPC ............ *A61K 35/28* (2013.01); *A01N 1/0215* (2013.01); *A01N 1/0221* (2013.01); *A01N 1/0226* (2013.01); *A01N 1/0284* (2013.01); *C12N 5/0663* (2013.01); *C12N 2501/24* (2013.01); *C12N 2523/00* (2013.01)

(58) Field of Classification Search
None
See application file for complete search history.

(56) References Cited

U.S. PATENT DOCUMENTS

2013/0017175 A1   1/2013   Bartholomew
2017/0151284 A1*  6/2017   Dalemans .............. A61P 29/00

FOREIGN PATENT DOCUMENTS

WO    2009114860      9/2009
WO    2016001846      1/2016
WO    WO 2016/001846  * 1/2016

OTHER PUBLICATIONS

Cryopreservation—Wikipedia pp. 1-7 downloaded Aug. 30, 2021.*
Capelli et al. Clinical grade expansion of MSCs, Immunology Letters 168 (2015) 222-227.
Chinnadurai et al. IDO-Independent Suppression of T Cell Effector Function by IFN-g-Licensed Human Mesenchymal Stromal Cells, The Journal of Immunology, 2014, 192: 1491-1501.
Chinnadurai et al. Cryopreserved Mesenchymal Stromal Cells Are Susceptible to T-Cell Mediated Apoptosis Which Is Partly Rescued by IFNc Licensing, Stem Cells 2016, 34:2429-2442.
Francois et al. Cryopreserved mesenchymal stromal cells display impaired immunosuppressive properties as a result of heat-shock response and impaired interferon licensing, Cytotherapy, 2012, 14, 147-152.
Galipeau et al. The mesenchymal stromal cells dilemma—does a negative phase III trial of random donor mesenchymal stromal cells in steroid-resistant graft-versus-host disease represent a death knell or a bump in the road? Cytotherapy, 2013, 15: 2-8.
Giri et al. Mesenchymal stromal cell therapeutic potency is dependent upon viability, route of delivery, and immune match, Blood Adv, 2020, 4(9):1987-1997.
Hanley et al. Manufacturing Mesenchymal Stromal Cells for Phase I Clinical Trials, Cytotherapy. 2013, 15(4): 416-422.
Horwitz et al. Mesenchymal Stromal Cells, Curr Opin Hematol, 2006, 13(6):419-425.
Krampera et al. Mesenchymal stromal cell 'licensing': a multistep process, Leukemia (2011) 25, 1408-1414.
Marquez et al. Mesenchymal stromal cells derived from various tissues: Biological, clinical and cryopreservation aspects, Cryobiology, 2015, 71, 181-197.
Mitchell et al., Rational, yet simple, design and synthesis of an antifreeze-protein inspired polymer for cellular cryopreservation, Chem Commun (Camb), 2015, 51(65): 12977-12980.
Moll et al. Do Cryopreserved Mesenchymal Stromal Cells Display Impaired Immunomodulatory and Therapeutic Properties? Stem Cells, 2014, 32(9): 2430-2442.

* cited by examiner

Primary Examiner — Maria G Leavitt
(74) Attorney, Agent, or Firm — Emory Patent Group (57) ABSTRACT

This disclosure relates to methods of preserving mesenchymal stromal/stem cells (MSCs) for use in clinical applications. In certain embodiments, this disclosure relates to methods of preserving MSCs comprising mixing MSCs with interferon-gamma prior to cryopreserving, freezing, or cooling the MSCs to a temperature below zero degrees Celsius.

8 Claims, 10 Drawing Sheets
Specification includes a Sequence Listing.

SEQUENCE LISTING

```
<160> NUMBER OF SEQ ID NOS: 1

<210> SEQ ID NO 1
<211> LENGTH: 136
<212> TYPE: PRT
<213> ORGANISM: Homo sapiens

<400> SEQUENCE: 1

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
            35                  40                  45

Ile Val Ser Phe Tyr Phe Lys Leu Phe Lys Asn Phe Lys Asp Asp Gln
        50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe
130                 135
```

METHODS OF PRESERVING MESENCHYMAL STEM CELLS

CROSS-REFERENCE TO RELATED APPLICATIONS

This application is the National Stage of International Application No. PCT/US2017/021523 filed Mar. 9, 2017, which claims the benefit of U.S. Provisional Application No. 62/305,644 filed Mar. 9, 2016. The entirety of each of these applications is hereby incorporated by reference for all purposes.

STATEMENT REGARDING FEDERALLY SPONSORED RESEARCH

This invention was made with government support under R01AI015416 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 16077US_ST25.txt. The text file is 2 KB, was created on Sep. 10, 2018, and is being submitted electronically via EFS-Web.

BACKGROUND

Mesenchymal stem cells can be derived from multiple tissue sources such as bone marrow, umbilical cord, adipose tissue, and placenta. Of these, bone marrow derived mesenchymal stem cells are the most commonly tested in clinical trials for their anti-inflammatory and regenerative properties. Mesenchymal stem cells in bone marrow maintain their hematopoietic niche, regulate marrow immune homeostasis, and can differentiate into bone, cartilage, and adipocytes. Despite their low frequency in marrow, mesenchymal stem cells can be expanded under standard cell culture conditions for use as a cellular pharmaceutical. Safety of mesenchymal stem cell infusions has been established in early phase clinical trials but clear demonstration of efficacy is an ongoing concern. Cryopreservation and long-term storage of mesenchymal stem cells may be a contributing factor. Thus, there is a need to identify improved methods for preserving mesenchymal stem cells.

Hanley et al. report cryopreservation of MSCs. Cytotherapy, 2013, 15(4): 416-422. See also Marquez et al. Cryobiology, 2015, 71, 181-197, Capelli et al., Clinical grade expansion of MSCs, Immunol Lett. 2015, 168(2):222-7.

Chinnadurai et al. report suppression of T cell effector function by IFN-gamma-licensed human mesenchymal stromal cells. J Immunol, 2014, 192:1491-1501. See also Krampera et al. Leukemia, 2011, 25, 1408-1414 and Chinnadurai et al. Stem Cells, 2016, 34(9):2429-42.

References cited herein are not an admission of prior art.

SUMMARY

This disclosure relates to methods of preserving mesenchymal stem cells for use in clinical applications. In certain embodiments, this disclosure relates to methods of preserving MSCs comprising mixing MSCs with interferon-gamma prior to cryopreserving, freezing, or cooling the MSCs to a temperature below zero degrees Celsius or lower.

In certain embodiments, the cooling temperature is less than −25, −50, −75, −100, or −150 degrees Celsius. In certain embodiments, the cooling temperature is not less than −25, −50, −75, −100, or −150 degrees Celsius.

In certain embodiments, mixing MSCs with interferon-gamma is at a concentration of about, less than, and/or more than 20 ng/mL. In certain embodiments, the interferon-gamma is at a concentration is between 10 and 30 ng/mL. In certain embodiments, the interferon-gamma is at a concentration is between 1.0 and 100 ng/mL.

In certain embodiments, mixing MSCs with interferon-gamma is for a duration of more than and/or less than 10, 20, 30, 40, 50, or 60 hours. In certain embodiments, mixing is for a duration of more than 1 hour. In certain embodiments, mixing is for a duration of more than 10 hours or more than 24 hours.

In certain embodiments, it is contemplated that preserved MSCs are washed and/or are substantially free of unbound interferon-gamma in the frozen mass. In certain embodiments, it is contemplated that interferon-gamma is bound to cell surface receptors on MSCs contained within a frozen mass of MSCs. In certain embodiments, it is contemplated that interferon-gamma is internalized by MSCs contained within a frozen mass of MSCs. In certain embodiments, it is contemplated that preserved MSCs comprise residual interferon-gamma and/or are contained within a frozen mass. In certain embodiments, it is contemplated that a composition of preserved MSCs includes exogenous interferon-gamma.

In certain embodiments, the MSCs are in or mixed with a cryoprotectant prior or during cooling. In certain embodiments, the cryoprotectant comprises a monosaccharide, a disaccharide, trehalose, glycerol, ethylene glycol, and propylene glycol, or combinations thereof. In certain embodiments, the cryoprotectant comprises L-proline, poly-L-lysine, a polyampholyte, succinylated poly-L-lysine, a protein comprising lysine and glutamic acid, a protein comprising lysine and aspartic acid, a polymer comprising amino and carboxylic acid groups wherein the mole fraction of carboxylic acid to amino groups is in excess or the mole percentage of carboxylic acid groups to the total of carboxylic acid and amino groups is between 40 and 80 percent.

In certain embodiments, the methods disclosed herein further comprise thawing the MSCs to a temperature above zero degrees Celsius or above or between 20 to 40 degrees Celsius providing thawed MSCs.

In certain embodiments, the methods disclosed herein further comprise mixing the thawed MSCs with interferon-gamma, interleukin-1beta, interleukin-1alpha, transforming growth factor-beta, interleukin-6, interleukin-10, prostaglandin-E2, hepatocyte growth factor, tumor necrosis factor-alpha, or combinations thereof.

In certain embodiments, methods disclose herein further comprise the steps of purifying, plating, passaging, and/or harvesting the thawed MSCs providing regenerated mesenchymal stem cells.

In certain embodiments, this disclosure contemplates using MSCs produced by methods disclosed herein, e.g., thawed MSCs having prior exposure to IFN-gamma and optionally regenerated, for medical applications and in medical preparations.

In certain embodiments, the disclosure relates to methods of treating or preventing a disease or medical condition comprising administering or transplanting an effective amount of a composition comprising MSCs made by the methods disclosed herein.

In certain embodiments, the disclosure relates to the production of a medicament comprising MSCs made by the methods disclosed herein for the use of treating or preventing a disease or medical condition.

BRIEF DESCRIPTION OF THE DRAWINGS

FIG. 3A shows data for Cryo mRNA expression of heat shock proteins HSP70A. Live (L) MSCs were subjected in to three treatments namely, Cytochalasin D (2 uM) for 2 hours to depolymerize actin cytoskeleton (AD-L), cultured in a 42C incubator for three hours to induce heat shock response (HS-L) and both (AD-HS-L). L, and HS-L MSCs were tested for the mRNA expression of heat shock proteins HSP70A. mRNA relative to GAPDH was evaluated by the quantitative SYBR green real time PCR. Delta-delta CT method was applied to calculate the fold induction of HSP70A over the Live (L) control. Freeze-thawing induced heat shock response and disruption of actin polymerization do not modulate human MSC's immunosuppressive properties.

FIG. 5A shows data on the dose dependent effect of Z-VAD-FMK treated thawed MSCs on T cell proliferation (CD3 Ki67). IFNgamma, Z-VAD-FMK, 3-Methyl adenine (3-MA) pretreated MSCs were cryopreserved and thawed to compare with live MSC's immunosuppressive potential. MSC populations (Live, Cryo and IFNgamma/Z-VAD-FMK/3-MA Cryo) were cocultured with SEB activated PBMCs in indicated ratios. PBMC and MSC numbers were kept constant and variable for escalating ratios. Four days post, T cell proliferation was measured by flow cytometry. IFNgamma prelicensing but not inhibitors of autophagy and caspase rescues frozen-thawed MSC's defective immunosuppressive properties

FIG. 6C shows data on the kinetics of % of CD3 CD8 CD107 IFNgamma T cells. SEB activated PBMCs were cocultured in the presence and absence of live, cryo and IFNgamma cryo MSCs. Twelve to fourteen hours prior to the indicated time point BFA, monensin and antibody to CD107 were added to the culture. Cells were subsequently stained with antibodies to CD3, CD8 and IFNgamma for flow cytometry.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

Interferon-gamma (IFNgamma) is also known as type II or immune interferon. Mature human IFNgamma exists as a non-covalently linked homodimer of 20-25 kDa. Human IFNgamma has about 90% amino acid (aa) sequence identity with rhesus IFNgamma, 59%-64% with bovine, canine, equine, feline, and porcine IFNgamma. The mature chain of human IFNgamma has SEQ ID NO: 1, QDPYVKEAENLKKYFNAGHSDVADNGTLFLGILKNWKEESDRKIMQSQIVSFYFKLFK NFKDDQSIQKSVETIKEDMNVKFFNSNKKKRDDFEKLTNYSVTDLNVQR KAIHELIQVM AELSPAAKTGKRKRSQMLF. In certain embodiments, IFNgamma refers to sequences having 30, 35, 40, 45, 50, 55, 60, 65, 70, 75, 80, 85, 86, 87, 88, 89, 90, 91, 92, 93, 94, 95, 96, 97, 98, or 99% or greater sequence identity or similarity to SEQ ID NO: 1.

Sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q.

The term "mesenchymal stromal cells" refers to the subpopulation of fibroblast or fibroblast-like nonhematopoietic cells with properties of plastic adherence and capable of in vitro differentiation into cells of mesodermal origin which may be derived from bone marrow, adipose tissue, umbilical cord (Wharton's jelly), umbilical cord perivascular cells, umbilical cord blood, amniotic fluid, placenta, skin, dental pulp, breast milk, and synovial membrane, e.g., fibroblasts or fibroblast-like cells with a clonogenic capacity that can differentiate into several cells of mesodermal origin, such as adipocytes, osteoblasts, chondrocytes, skeletal myocytes, or visceral stromal cells. The term, "mesenchymal stem cells" refers to the cultured (self-renewed) progeny of primary mesenchymal stromal cell populations.

Bone marrow derived mesenchymal stromal cells are typically expanded ex vivo from bone marrow aspirates to confluence. Certain mesenchymal stromal/stem cells share a similar set of core markers and properties. Certain mesenchymal stromal/stem cells may be defined as positive for CD105, CD73, and CD90 and negative or low for CD45, CD34, CD14, and have the ability to adhere to plastic. See Dominici et al. Minimal criteria for defining multipotent mesenchymal stromal cells. The International Society for Cellular Therapy position statement. Cytotherapy, 2006, 8(4):315-7.

Adipose tissue-derived multipotent stem cells (ADMSCs) are multipotent, undifferentiated, self-renewing progenitor cell population isolated from adipose tissue. One method to isolate ADSCs from fat tissue relies on a collagenase digestion, followed by centrifugal density gradient separation. In vitro, ADMSCs typically display a spindle-shaped morphology and lack the intracellular lipid droplets as seen in adipocytes. Isolated ADMSCs are typically expanded in monolayer cultures with a growth medium containing fetal bovine serum and/or human platelet lysate. ADMSCs have the stem cell-specific surface markers, such as CD90, CD105, CD73, and lack the expression of the hematopoietic markers CD45 and CD34.

As used herein, and unless the context clearly suggests otherwise, the term "MSCs" refers to multipotent stem cells such as mesenchymal stromal cells, mesenchymal stem cells, and adipose tissue-derived multipotent stem cells.

As used herein, the term "frozen" refers to the solid state of matter wherein molecules within the matter are typically in liquid form at or above room temperature. It is contemplated to include material that is partially or entirely frozen.

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

Manufacturing of Mesenchymal Stem Cells

Bone marrow mononuclear cells can be isolated from bone marrow base on density. See Hanley et al. Cytotherapy, 2013, 15(4): 416-422. See also Capelli et al., Clinical grade expansion of MSCs, Immunol Lett. 2015, 168(2):222-7. Bone marrow mononuclear cells can be plated at e.g. at $5 \times 10^5$ cells per cm$^2$ or less on a growth medium containing 5% human platelet lysate. After several days, fresh medium can be added. When the cells are greater than 70% confluent, they can be split at a 1:4 flask ratio. The cells can be harvested after initiation, but optimally before passage 5 or 30 cell doublings. To harvest, the medium maybe aspirated from the flasks and the cells are washed and placed in suspension. Medium is then added to the cells that are harvested. Before cryopreservation, the mesenchymal stem cells may be centrifuged and washed. The cells may be resuspended in a medium at about half the final freeze volume. After placing the cells on ice, freeze media is added. Cells are typically cryopreserved using a controlled-rate freezer and freezing ramps.

Cryopreservation—IFNgamma Exposure

As of 2016, there are no clinical trials using intravenous infused mesenchymal stem cells, which have met their primary endpoint of efficacy. Yet, there are numerous preclinical studies in robust animal models of disease demonstrating the substantial utility of mesenchymal stem cells for an array of ailments spanning immune disorders to tissue repair. This raises the question of what are the drivers of this discrepancy in outcomes. Most animal studies typically utilize syngeneic mesenchymal stem cells (akin to autologous in humans), but also allogenic as well and this is reflected in human studies. A near universal discriminator although is that virtually all animal studies (murine being the dominant) typically utilize metabolically, fit, log phase of growth mesenchymal stem cells straight from culture, whilst near universally human trials utilize cryobanked mesenchymal stem cells administered to subjects within hours following retrieval from cryostorage and thaw.

This substantial methodological difference may explain, in part, the distinct outcomes between preclinical studies and pivotal human trials. Frozen-thawed mesenchymal stem cells display an altered physiological state in the 24 hours following retrieval from cryostorage, which significantly alters their properties as a pharmaceutical agent when given intravenously. The mechanistic understanding of freeze-thaw induced alterations in mesenchymal stem cell biochemistry could inform on remedies to restore desirable pharmaceutical properties including potency, distribution and persistence in vivo following intravenous transfusion in subjects.

Cryo mesenchymal stem cells are susceptible to contact-dependent apoptosis when cocultured with activated T-cells. Mesenchymal stem cell mediated induction of tolerance on T cells is partly through contact dependent cell surface factors such as PDL1, PDL2, CD95L, ICAM-1 and VCAM-1 both in vivo and in vitro. Cryo mesenchymal stem cells may be compromised in their suppressive properties due to their poor survival upon contact with inflammatory immune responders. In addition, mesenchymal stem cells distribute and bind to the capillaries of lungs immediately post infusion where it has been proposed that they interact with tissue resident and infiltrating lymphocytes and monocytes. The shortened in vivo persistence of Cryo mesenchymal stem cells in lungs may be partly/entirely due to their interaction with lytic immune responders.

Freeze-thawing affects polymerization of actin also induces a heat shock response in mesenchymal stem cells. Depolymerization of actin cytoskeleton in actively growing mesenchymal stem cell attenuates their binding in vivo. Interestingly, actin depleted mesenchymal stem cells still inhibit T proliferation in vitro suggesting that the mechanisms of freeze-thawing induced defect on binding of mesenchymal stem cells and immunosuppressive properties are distinguishable to each other. In addition, heat shocked live mesenchymal stem cells with or without actin depletion still inhibit T cell responses comparable to control live mesenchymal stem cells suggesting that the heat shock response is a passive bystander effect of freeze-thawing and does not obviate immunosuppressive properties of mesenchymal stem cells on its own. Altogether, identically thawed mesenchymal stem cells retain their immune suppressive effect on T-cell proliferation if they are separated by a physical barrier suggestive that the heat shock response and cytoskeletal disruption in themselves do not abort their suppressor function, but rather that frozen-thawed mesenchymal stem cells and granzyme+ T-cells make poor bedfellows. Thus, freeze-thawing induced alterations in the plasma membrane, intracellular pH, and mitochondrial depolarization likely potentiate susceptibility of mesenchymal stem cells to T cell mediated killing and may also promote sensitivity to complement-mediated lysis.

Mesenchymal stem cells are responsive to IFNgamma derived from host lymphoid effector cells and deploy immunosuppressive properties and in vitro and in vivo studies demonstrated that both infusion of IFNgamma receptor KO MSCs and absence of IFNgamma abolishes mesenchymal stem cell efficacy. Frozen-thawed mesenchymal stem cells are not only susceptible to lysis by lymphoid cytotoxic mediators, but also display hyporesponsivess to IFNgamma, which collectively suggest that freeze-thawing would greatly affect transient therapeutic effect of mesenchymal stem cells in the recipient.

Frozen-thawed mesenchymal stem cell preparations contain a higher percentage of apoptotic cells (around 10-15%) than live counterparts. Despite normalizing for viability of live and frozen-thawed cells in immunosuppressive and in vivo binding assays, dysfunctionality of thawed cells was observed suggesting an intrinsic defect. However, frozen-thawed mesenchymal stem cells inhibit T cell proliferation at high MSC:T-cell ratios, which likely provide a straight-forward explanation for discrepant results from other studies that failed to observe inferior functionality of frozen-thawed cell. Clinical efficacy may possibly be achieved by infusing higher doses of thawed mesenchymal stem cells to palliate for their blunted function, however there are practical logistic limits considering that most clinical trials use to 1-10 million mesenchymal stem cells/kg (typically <2 million cells/kg) in single or multiple infusions.

Mesenchymal stem cells undergo reversible changes post freeze-thaw, which can affect their pharmaceutical and biological properties in the hours following their retrieval from cryostorage. Frozen-thawed human mesenchymal stem cells increase a blood clotting response and induce acute instant blood-mediated inflammatory reaction (IBMIR) in vitro, are susceptible to complement-mediated lysis and have a blunted ability to support chondrocyte growth when delivered in vivo. Whether freeze-thawing leads to shedding of GPI-anchored molecules, which play a role in complement deactivation was tested. Freeze-thawing or IFNgamma pre-treatment do not alter surface expression of GPI anchored molecules on mesenchymal stem cells relative to fresh cells suggesting that alternate mechanisms are at play leading to MSC susceptibility to complement.

DMSO for cryopreservation of stem cells has been successfully used, notwithstanding its association with transfusion associated clinical side effects. To mitigate the negative effect on freeze-thaw on MSC function, it was tested whether alternative-freezing solutions using best practice controlled rate freezing methods could rescue the susceptibility of mesenchymal stem cells to T-cell driven apoptosis.

Considering the potential role of induced autophagy and priming of caspase activation post thaw in mesenchymal stem cell lysis, it was tested whether adding specific inhibitors to both processes as part of freezing media as well as post thaw would increase mesenchymal stem cell resilience. Neither the use of 3-Methyl Adenine nor Z-VAD-FMK negated mesenchymal stem cells susceptibility to T-cell lysis. However, preactivation of mesenchymal stem cells with IFNgamma before freezing led to an IDO-driven resistance to in vitro T-cell lysis post thaw.

The tissue tropism of intravenously transfused mesenchymal stem cells requires adhesion molecule mediated arrest within the vasculature of respective tissue and eventual extravasation. Human mesenchymal stem cells express cell surface adhesive molecules, including: α4, α5, β1 integrin components and CD63. Although their role in tissue homing is unclear, thawing does not lead to reduced expression on cell surface. In addition, IFNgamma prelicensing does not modulate expression of these molecules except for increase of ICAM-1 and VCAM-1. These may play a role in IFN-gamma-driven immune suppression in vitro. It is contemplated that IFNgamma activated frozen-thawed mesenchymal stem cells will lead to improved pharmaceutical effect in disease models.

Experiments disclosed herein indicated that thawed mesenchymal stem cells deploy an altered physiology. Frozen-thawed mesenchymal stem cells are susceptible to lysis by activated T cells. This phenomenon is reversible since culture rescue of frozen-thawed mesenchymal stem cells fully regain their fitness and resist bystander lysis by activated T-cells. Moreover, culture rescue for as little as 24 hours fully restores immune modulatory and biodistributive properties of mesenchymal stem cells as well. Pharmacological effects of mesenchymal stem cells in vivo are likely transient considering the lack of sustained engraftment, as they neither replicate in vivo nor form ectopic tissue. This latter observation suggest that akin to prevalent preclinical animal data, that the use of metabolically fit human mesenchymal stem cells may allow for deployment of their full therapeutic potential as part of clinical trials thereby enhancing a positive bias toward validation of efficacy.

Methods of Use

In certain embodiments, this disclosure contemplates using MSCs produced by methods disclosed herein, e.g., thawed MSCs having prior exposure to exogenous IFN-gamma, for medical applications and in medical preparations. In certain embodiments, this disclosure relates to methods of treating a disease or condition comprising administering an effective amount of a composition comprising MSCs to a subject in need thereof, wherein the MSC are frozen and thawed MSCs and wherein the MSCs were mixed with interferon-gamma prior to freezing or cooling the cells.

In certain embodiments, the disclosure relates to methods of treating or preventing a disease or medical condition comprising administering or transplanting an effective amount of a composition comprising MSCs made by the methods disclosed herein.

In certain embodiments, the disclosure relates to the production of a medicament comprising MSCs made by the methods disclosed herein for the use of treating or preventing a disease or medical condition.

In certain embodiments, the disease or condition is selected from hematological diseases, GVHD, diabetes, inflammatory diseases, and diseases in the liver, kidneys, and lungs, cardiovascular, bone and cartilage, neurological, and autoimmune diseases. In certain embodiments, the disease or condition is a bone degenerative disease such as osteogenesis imperfect. In certain embodiments, the disease or condition is cartilage defects. In certain embodiments, the disclosure contemplates the combined administration of MSCs disclosed herein with hematopoietic stem cell transplantation. In certain embodiments, the disease or condition is Crohn's disease. In certain embodiments, the disease or condition is multiple sclerosis. In certain embodiments, the disease is acute or chronic graft versus host disease. In certain embodiments, the disease is systemic lupus erythematosus. In certain embodiments, the disease is liver cirrhosis In certain embodiments, it is contemplated that MSCs support hematopoiesis and enhance marrow recovery following chemotherapy or radiotherapy. In certain embodiments, the disclosure contemplates methods of treating a subject with cancer by administering/transplanting MSCs prepared by processes disclosed herein prior to, during, or following chemotherapy or radiotherapy.

In certain embodiments, the disclosure contemplates methods of treating a subject with a hematologic cancer e.g., lymphoma, myeloma, and some leukemia, by administering/transplanting a combination of MSCs prepared by processes disclosed herein and hematopoietic stem cells optionally in further combination with corticosteroids in order facilitate the engraftment of HSCs to reduce GVHD, lessen GVHD severity. In certain embodiments, it is contemplated that peripheral blood mononuclear cells (PBMNCs) of a donor are collected by leukapheresis after pretreatment with granulocyte colony-stimulating factor (GCSF). In certain embodiments, the products of leukapheresis may be further purified by selecting cells that are CD34+ hematopoietic stem cells (HSCs) which are then combined with MSCs produced by processes disclosed herein and administered/transplanted to a subject. In certain embodiments, the MSCs are infused following the transplantation of HSCs.

In certain embodiments, the disclosure contemplates methods of treating a subject with ischemic heart diseases, myocardial infarction, coronary artery disease (CAD), refractory angina, ischemic cardiomyopathy (ICM), or congestive heart failure by administering/transplanting a combination of MSCs prepared by processes disclosed herein optionally in combination with BM-derived endothelial progenitor cells (EPCs). In certain embodiments, the disclosure contemplates intracoronary injection or transendocardial injection of MSCs optionally in combination with other stem cells. In certain embodiments, the disclosure contemplates improved contractility.

In certain embodiments, the disclosure contemplates methods of treating a subject with multiple sclerosis (MS), amyotrophic lateral sclerosis (ALS), or spinal cord injury by administering/transplanting MSCs prepared by processes disclosed herein. In certain embodiments, the disclosure contemplates intravenously or intrathecally administration. In certain embodiments, the disclosure contemplates local injection of MSC in the spinal cord or nearby area.

In certain embodiments, the disclosure contemplates methods of treating a subject with bone and cartilage disease, or osteogenesis imperfect, osteoarthritis by administering/transplanting MSCs prepared by processes disclosed herein. In certain embodiments, the disclosure contemplates reduction of the degeneration of articular cartilage accompanied by reduced subchondral bone sclerosis and synovial inflammation. In certain embodiments, the disclosure contemplates stimulating the regeneration of cartilage and halting the progressive destruction of joints. In certain embodiments, the disclosure contemplates intra-articular injection, e.g., in the area of the knee.

In certain embodiments, the disclosure contemplates methods of treating a subject with a lung injury, respiratory distress syndrome, idiopathic pulmonary fibrosis, kidney disease, liver injury, liver failure, or liver cirrhosis by administering/transplanting MSCs prepared by processes disclosed herein. In certain embodiments, the disclosure contemplates intravenously administration.

In certain embodiments, the disclosure contemplates methods of treating a subject with kidney injuries after transplantation or other organ transplant by administering/transplanting MSCs prepared by processes disclosed herein. In certain embodiments, the disclosure contemplates preventing renal organ failure. In certain embodiments, the disclosure contemplates methods using autologous MSCs to induce tolerance in living-donor kidney transplant recipients. In certain embodiments, the disclosure contemplates ex-vivo expanded mesenchymal stem cells to repair the kidney and improved function in cisplatin-induced acute renal failure in patients with solid organ cancers.

In certain embodiments, the disclosure contemplates methods of treating a subject with refractory aplastic anemia (AA) by administering/transplanting MSCs prepared by processes disclosed herein.

In certain embodiments, the MSCs are transplanted, administered IV, IM, or directly in an area of desired tissue or bone growth.

In certain embodiments, subject is selected from the group consisting of human, canine, feline, equine, or lagomorph.

In certain embodiments, MSCs are allogeneic, autologous, or syngeneic to the subject.

In certain embodiments, the MSC composition consists essentially of mesenchymal stem cells and saline. In certain embodiments, the MSCs may be incorporated into a polymer matrix, collagen, or gel (hydrogel) matrix prior to administration or transplantation. In certain embodiments, the MSCs may be contained in a syringe.

In certain embodiments, the disclosure contemplates a dose of about $1 \times 10^6$ cell/kg or between $1 \times 10^5$ and $1 \times 10^7$ cell/kg of the subject, weekly. In certain embodiments, MSC composition includes mesenchymal stem cells and saline at a concentration of no more than 500,000 cells per ml. In certain embodiments, MSC composition includes mesenchymal stem cells and saline at a concentration of no more than 100,000 cells per ml.

In certain embodiments, MSCs are harvested from bone marrow. In certain embodiments, MSC are harvested from placental tissue. In certain embodiments, MSCs are harvested from dental tissue. In certain embodiments, MSCs are harvested from testicle tissue. In certain embodiments, MSCs are harvested from uterine tissue. In certain embodiments, MSCs are harvested from umbilical cord tissue. In certain embodiments, MSCs are harvested from skin tissue.

EXAMPLES

Figure 1A:
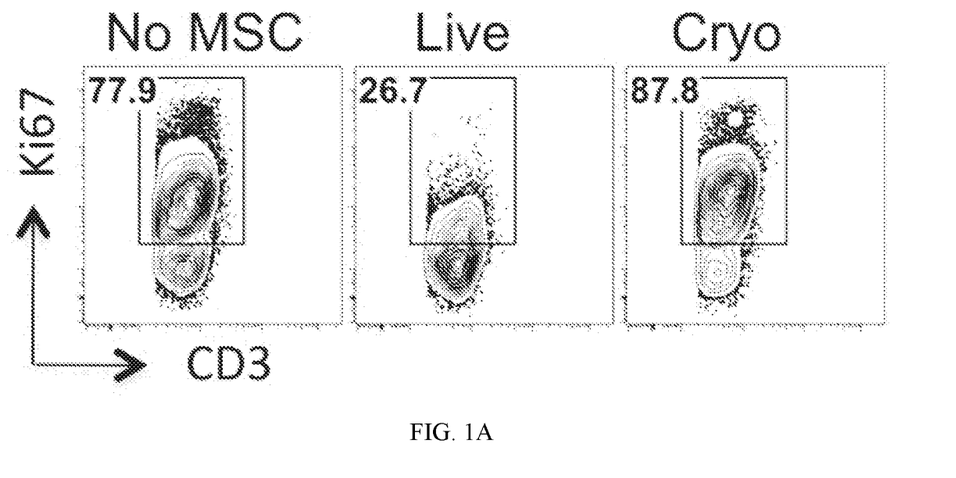
FIG. 1A shows representative FACS plot indicating frozen-thawed human MSCs display cell contact-dependent attenuated immunosuppressive properties on T cells. PBMCs co-cultured in the presence and absence of MSCs derived from actively growing culture (Live) or thawed from cryopreservation (Cryo) were stimulated with SEB. 4 days post, T cell proliferation was measured by Ki67 intracellular staining.
Figure 1B:
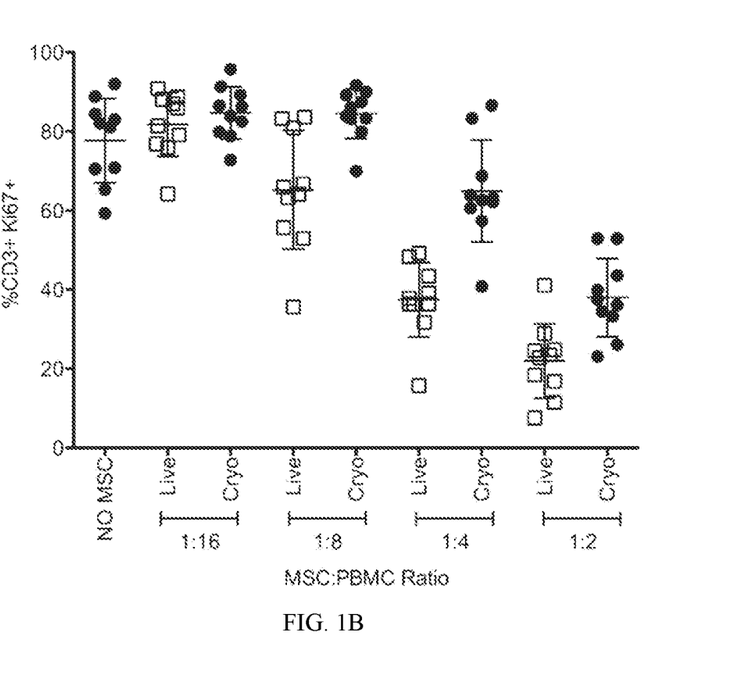
FIG. 1B shows data on the cumulative % of T cell proliferation (CD3+Ki67+) in the presence of variable MSC and PBMC ratio. Cumulative is plotted from multiple independent experiments tested with unique PBMC and MSC donors.
Figure 1C:
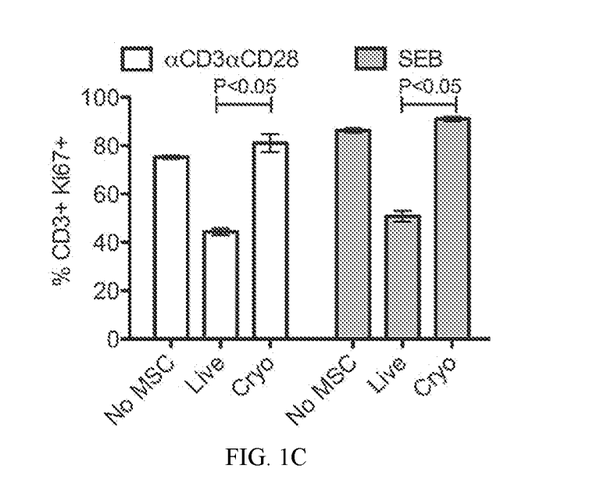
FIG. 1C shows data for Live and Cryo MSCs co-cultured with SEB and aCD3aCD28 activated PBMCs. Four days post culture, T cell proliferation was evaluated. Live and cryo MSCs were cultured with SEB activated T cells in a contact and non-contact dependent co-culture and transwell system.
Figure 1D:
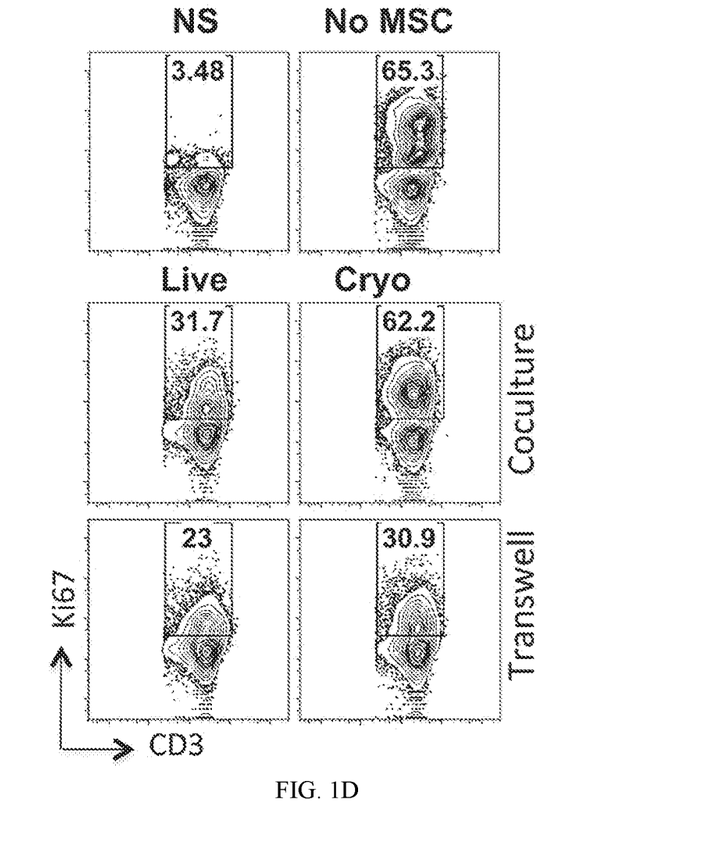
FIG. 1D shows a representative FACS plot (CD3 and Ki67) in the co-culture and transwell system.
Figure 1E:
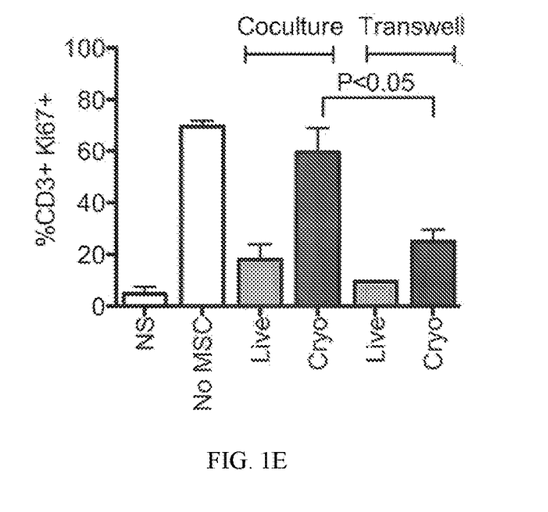
FIG. 1E shows data of cumulative % of T cell proliferation.

Defective Inhibition of T Cell Proliferation by Frozen-Thawed Human Mesenchymal Stem Cells is Cell Contact Dependent The immunosuppressive effect of bone marrow derived human mesenchymal stem cells obtained from both actively growing and frozen-thawed cultures analyzed (Live and Cryo MSCs respectively) were analyzed. Results of multiple (n=10) experiments with independent mesenchymal stem cell donor pairs (Live and Cryo) demonstrate that Live MSCs inhibit SEB activated Ki67+ T cell proliferation more efficiently than Cryo MSCs (% CD3+Ki67+: No MSC (78±11), Live MSC (38±9), Cryo MSC (65±13)) (FIG. 1B). Although the inhibitory effect of Live and Cryo MSCs were observed in a dose dependent manner, Live MSCs are superior to Cryo MSCs in inhibiting T cell proliferation at all MSC:T cell ratio tested (FIG. 1B). T cells in PBMC preparations can be activated either with SEB or aCD3aCD28 coated beads while both of these stimulants induce T cell activation in a distinct manner. In order to define the effect of distinct modes of T cell activation on Live and Cryo MSC's comparative veto function, SEB and aCD3aCD28 activated PBMCs were cocultured in the presence and absence of Live and Cryo MSCs. Experiments indicate that the functional defect of Cryo MSC's in attenuating T cell proliferation is independent of the mode of T cell activation (FIG. 1C). MSCs inhibit T cells both by contact and non-contact dependent mechanisms. Whether the defect in immunosuppressive properties of MSC is due to either contact or non-contact interaction with immune responders was investigated. Activated PBMCs were cultured with/without Live or Cryo MSCs using either direct coculture or coculture in which the T cells and MSC were separated by a two-chamber transwell system. Cryo MSCs inhibit T cell proliferation more efficiently in the transwell culture when compared to coculture system (% CD3+Ki67+: No MSC (70±2), Cryo MSC-Coculture (60±10), Cryo MSC-Transwell (25±5)) (FIG. 1E). This data suggests that activated PBMCs blunted the immunosuppressive properties of Cryo MSCs through a direct contact dependent interaction.

Figure 2A:
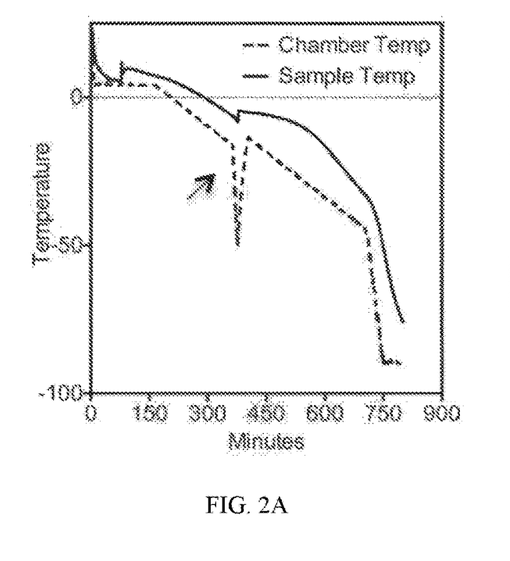
FIG. 2A illustrates a freezing program that was used to cryopreserve MSCs in a step down freezer. Chamber and sample temperature during step-down freezing is shown. An arrow shows alignment of "heat of fusion" between chamber and sample temperature. Additional data indicates freeze-thawing attenuates immunosuppressive properties of human MSCs independent of freezing methods.
Figure 2B:
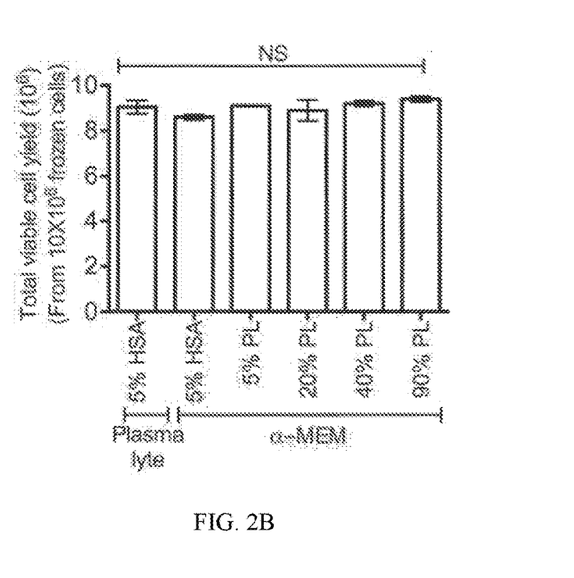
FIG. 2B shows data of total viable cell yield when Live or cryopreserved MSCs with the indicated formulations of cryoprotectant were thawed.
Figure 2C:
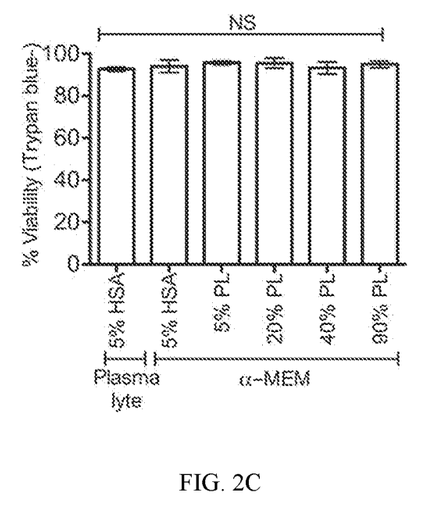
FIG. 2C shows data of Trypan blue viability.
Figure 2D:
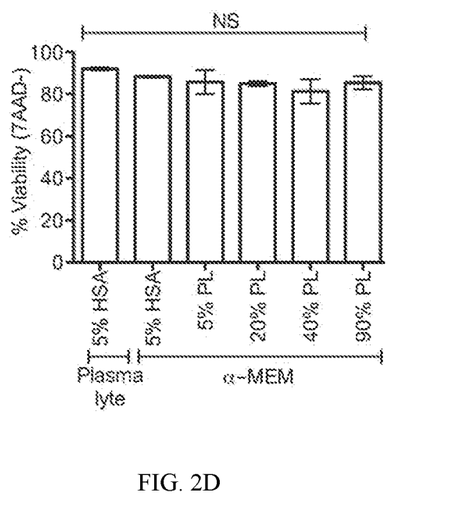
FIG. 2D shows data of 7-AAD negative viability.
Figure 2E:
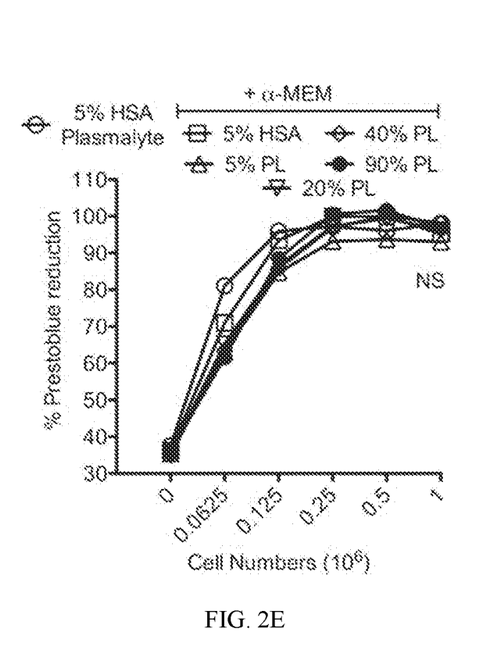
FIG. 2E shows data of Prestoblue reduction potential.
Figure 2F:
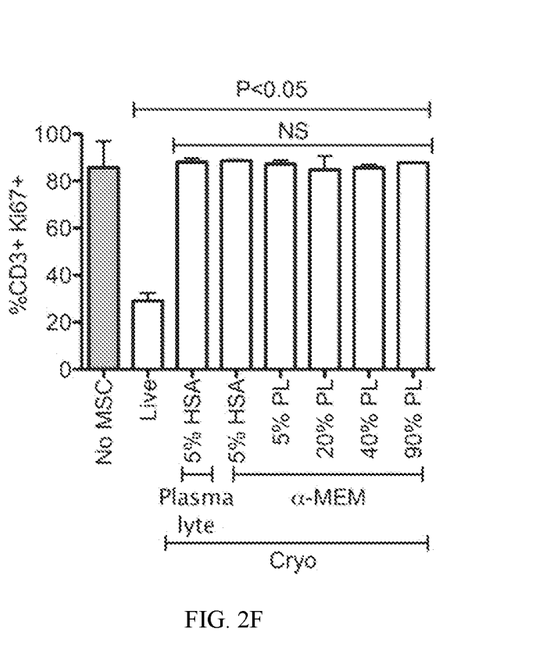
FIG. 2F shows data on T cell proliferation (% CD3 Ki67) measured by flow cytometry four days post culture. Cryo MSC populations were cocultured with SEB activated PBMCs and Live MSCs were used as controls.
Figure 2G:
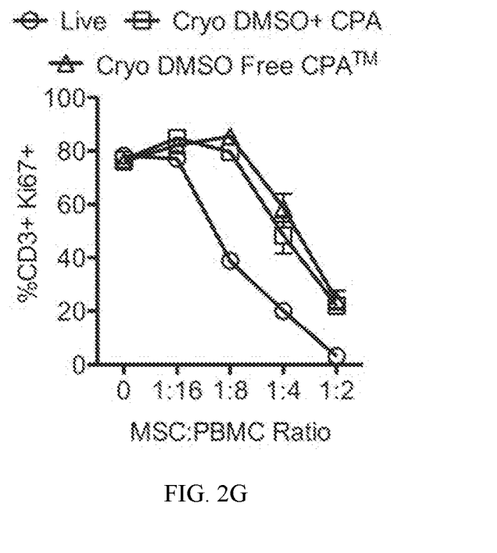
FIG. 2G shows data for Live or Cryo MSCs cryopreserved with 10% DMSO or DMSO free cryoprotectant.
Figure 2H:
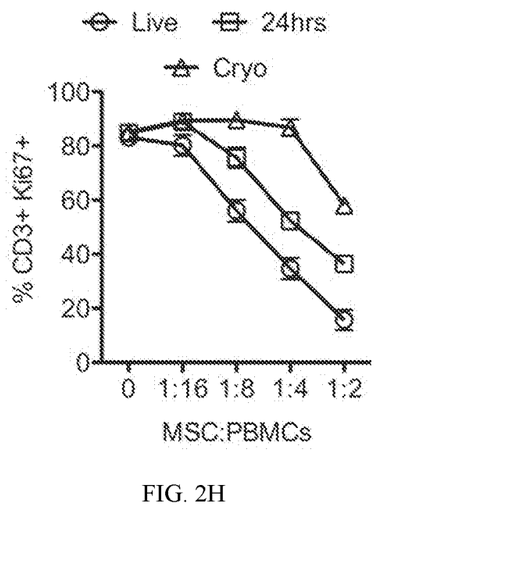
FIG. 2H shows data for live, thawed and 24-hour culture rescued MSCs that were and subjected to test their inhibitory effect on T cell proliferation. T cell proliferation was measured 4 days post culture.

Alternative Cryopreservation Methods and Formulations do not Rescue Frozen-Thawed Immunosuppressive Defects of Mesenchymal Stem Cells Research laboratories routinely use cell-freezing containers with isopropanol to cryopreserve mammalian cells in mechanical freezer while clinical stem cell storage facilities typically use controlled rate freezers. Although both of these methods of cryopreservation yield comparable clinical outcome with hematopoietic stem cells, effects on functionality post freeze-thaw of mesenchymal stem cells are unknown. The effect of a controlled freezing program on functionality post freeze-thaw of mesenchymal stem cells was tested (FIG. 2A). Standard media formulation for hematopoietic stem cell freezing is 5% HSA and 10% DMSO diluted in Plasmalyte. Considering that hPL is utilized for culture expansion and production of pharmaceutical grade MSCs, its use was tested in freeze media formulations as a substitute for human serum albumin along with controlled freezing conditions. Addition of various concentration (5%-90%) of hPL in cryopreservation media did not significantly enhance mesenchymal stem cell recovery (FIG. 2B), viability (FIG. 2C, 2D) and metabolic activity (FIG. 2E) post freeze-thaw. In addition, MSCs thawed from cryopreserved cultures containing platelet lysate display attenuated immunosuppressive properties compared to Live MSCs (% CD3+ Ki67+: No MSC (86±11), Live MSC (30±3), Cryo MSCs (5% HSA in α-MEM (88±2), 5% HSA in PL (89±1), 5% PL (87±2), 20% PL (85±6), 40% PL (86±2), 90% PL (87±1))) (FIG. 2F). Mesenchymal stem cells frozen-thawed from cryopreserved cultures containing DMSO-free cryoprotectant are defective in attenuating T cell proliferation as well (FIG. 2G), suggesting that use of controlled rate freezing methods and substitution of HSA with hPL and DMSO with alternates do not improve upon standard methodologies. However, sub culturing mesenchymal stem cells post freeze-thaw for at least 24 hours rescues their immunosuppressive properties (FIG. 2H) suggesting that freeze-thaw induced cellular defects are reversible.

Figure 3A:
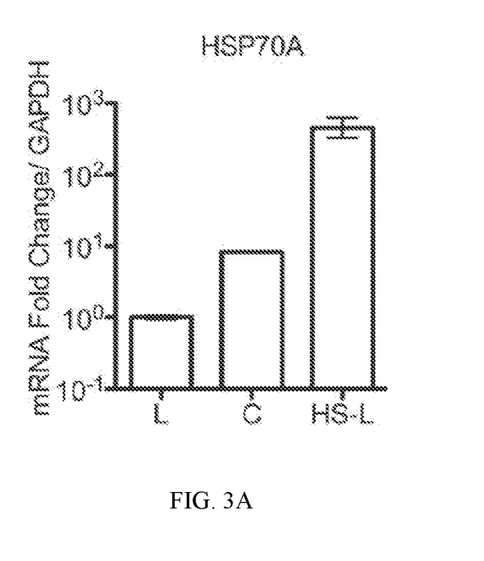
Figure 3B:
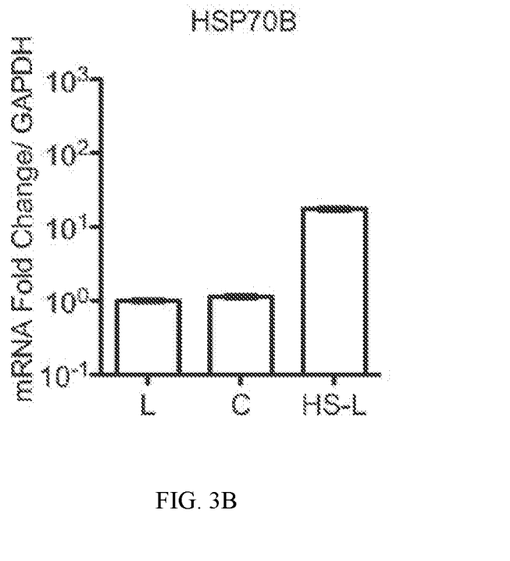
FIG. 3B shows data for HSP70B.
Figure 3C:
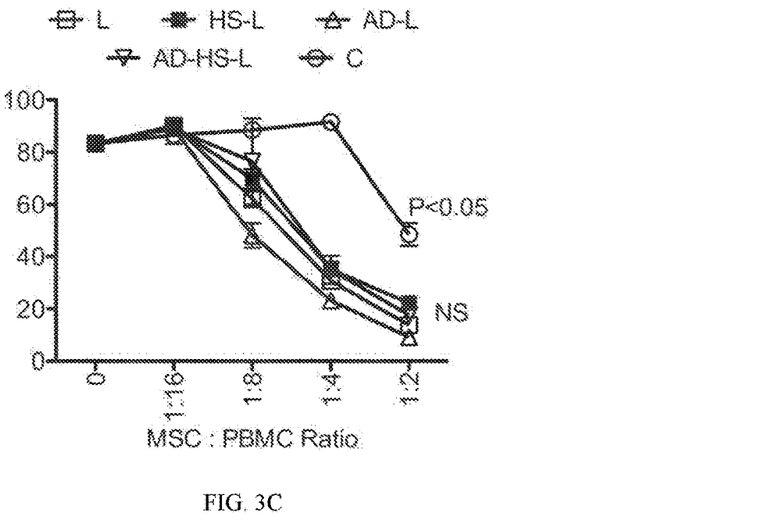
FIG. 3C shows data of dose dependent effect of MSCs on of T cell proliferation (CD3 Ki67). MSCs derived from conditions L, C, HS-L, AD-L, AD-HS-L were cocultured with Staphylococcal enterotoxin B (SEB) activated PBMCs with the indicated ratios for 4 days. T cell proliferation was measured by Ki67 intracellular staining.

Heat Shock Response and Actin Depolymerization Effects on Immunosuppressive Properties of Mesenchymal Stem Cells Freeze-thawing induces a molecular genetic heat shock response and depolymerizes cytoskeleton structure in mesenchymal stem cells. Whether freeze-thaw induced heat shock response and/or defective actin polymerization affect immunosuppressive properties of mesenchymal stem cells independently of freeze/thaw cycle was investigated. Incubation of mesenchymal stem cells in an incubator set at 42° C. induces HSP70A and HSP70B mRNA in freshly cultured Live MSCs (FIGS. 3A and 3B). As demonstrated previously, Cytochalasin D-treatment depolymerizes actin cytoskeleton structures, shrinks dendrites and eventually circularizes mesenchymal stem cells. Both heat shocked and cytochalasin D treated MSCs inhibit T cells similar to control cells (FIG. 3C). In addition, combined treatment of heat-shock and actin depolymerization do not confer attenuated immunosuppressive properties to MSCs (% CD3+Ki67+: No MSC (83±1), Live MSCs (30±1), Cryo MSCs (91±1), actin depleted Live MSCs (23±2), heat shocked Live MSCs (35±2), actin depleted and heat-shocked Lived MSCs (35±5)) (FIG. 3C) suggesting that freeze-thaw defect in mesenchymal stem cells in vitro immune suppression is independent of HS and F-actin cytoskeletal structure and that additional anomalies conferred by cell thawing are in play.

Figure 4A:
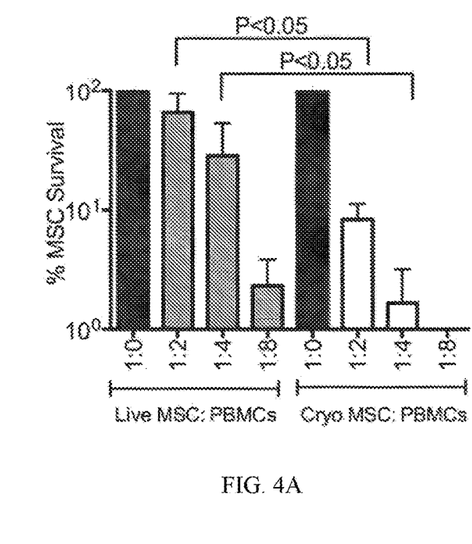
FIG. 4A shows data on a dose dependent effect of activated PBMCs on Live and Cryo MSC's survival. CFSE labeled Live and Cryo MSCs were cocultured with Staphylococcal enterotoxin B (SEB) activated PBMCs in indicated ratios. Microscopic images show the survival of CFSE labeled Live and Cryo MSCs in the coculture. Nuclei were stained with DAPI. Plate bound MSCs from the coculture were trypsinized and event counts were recorded in flow cytometry with the normalization of counting beads. Live and Cryo MSC count in the absence of PBMCs were used for normalization and calculation of % survival of Live and Cryo MSCs in the presence of PBMCs. Frozen-thawed MSCs are susceptible to lysis by activated T cells.
Figure 4B:
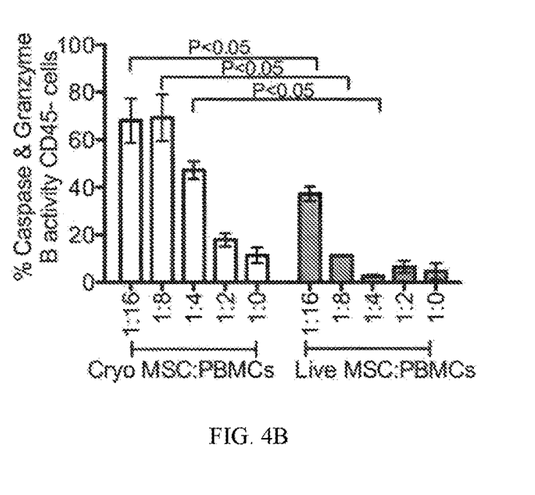
FIG. 4B shows data on the dose dependent effect of activated PBMCs on the serine protease activity in Live and Cryo MSCs. Serine protease activity was measured on Live and Cryo MSCs cocultured with/without activated PBMCs.
Figure 4C:
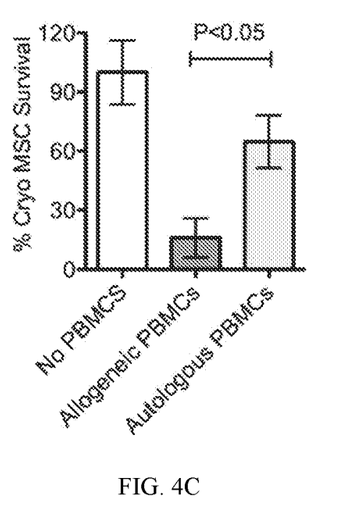
FIG. 4C shows data on % survival of CFSE labeled thawed MSCs cocultured with autologous and allogeneic PBMCs were shown.
Figure 4D:
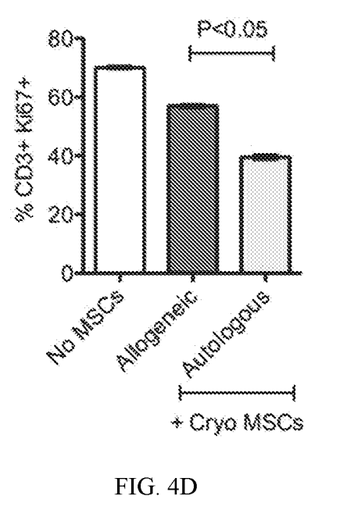
FIG. 4D shows data on the effect of Cryo MSCs in inhibiting autologous and allogeneic T cell proliferation (CD3 Ki67).
Figure 4E:
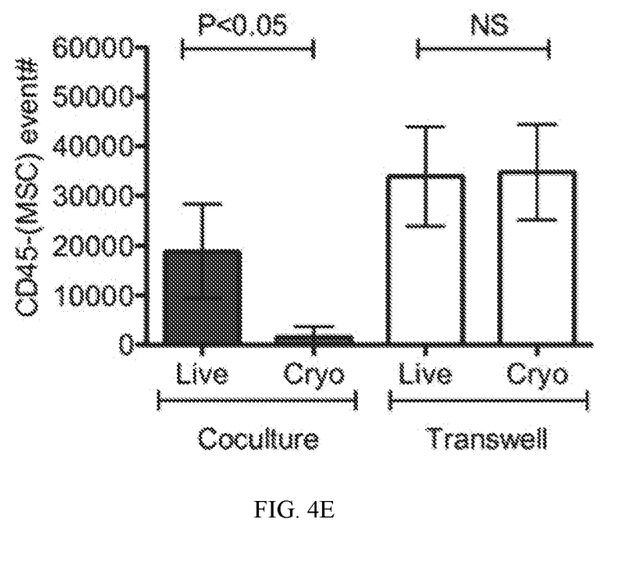
FIG. 4E shows data on the relative CFSE count of Live and Cryo MSCs in the presence of activated PBMCs cocultured or separated by a transwell system.

Frozen-Thawed Mesenchymal Stem Cells are Susceptible to Lysis by Activated PBMCs To further decipher the mechanism of attenuated immunosuppressive activity by Cryo MSCs, microscopic analysis of Cryo and Live MSCs (CFSE labeled) was performed in culture with activated PBMCs. Cryo MSCs were lysed in coculture with activated allogeneic PBMCs. In order to quantify the magnitude of lysis by activated PBMCs, CFSE+ Live and Cryo MSCs, retrieved upon coculture with activated PBMCs, were counted using flow cytometer with counting bead normalization to calculate the absolute numbers of live MSC per culture. Activated PBMCs lyse Cryo MSCs more so than actively growing live counter parts and this effect is dose dependent on the ratio of MSCs and activated PBMCs (% survival of Live (65±28%) or Cryo (8±2%) MSCs upon coculture with activated PBMCs) (FIG. 4A). Cytotoxic lymphocytes mediate cell killing by activating granzyme B driven cell death. To measure this effect in MSCs, a single cell cytotoxic assay was performed reflecting serine protease activity. Cryo MSCs cultured with activated PBMCs exhibit higher level of serine protease activities compared to actively growing live MSCs suggesting that activated PBMC mediated killing of Cryo MSCs (% serine protease activities in Live (11±1%) or Cryo (69±10%) MSCs upon coculture with activated PBMCs) (FIG. 4B). The effect of autologous vs allogeneic activated PBMCs on thawed MSCs were compared. Although Cryo autologous MSCs are also susceptible to lysis upon culture with activated PBMCs, the lysing effect is substantial less than that seen with coculture of MHC mismatched MSC:PBMC (% survival of autologous (60±13%) and allogeneic (16±10%) Cryo MSCs) (FIG. 4C). The inhibitory effect of thawed autologous and allogeneic MSCs on T cell proliferation were tested. Cryo MSCs are superior to allogeneic MSCs in inhibiting T cell proliferation (FIG. 4D). Next, the lysis of Cryo MSCs by activated allogeneic PBMCs in a transwell system was investigated. Cryo MSCs show statistically significant better survival following coculture with activated PBMCs in a transwell system than Cryo MSCs indirect contact with activated T cells (FIG. 4E).

Figure 5A:
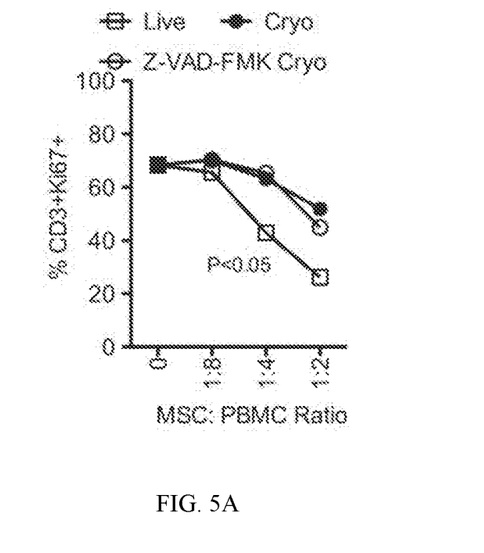
Figure 5B:
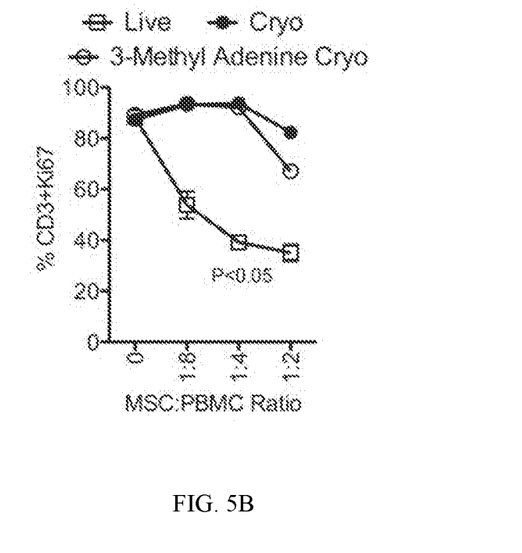
FIG. 5B shows data on the dose dependent effect of 3-MA treated thawed MSCs on T cell proliferation (CD3 Ki67).
Figure 5C:
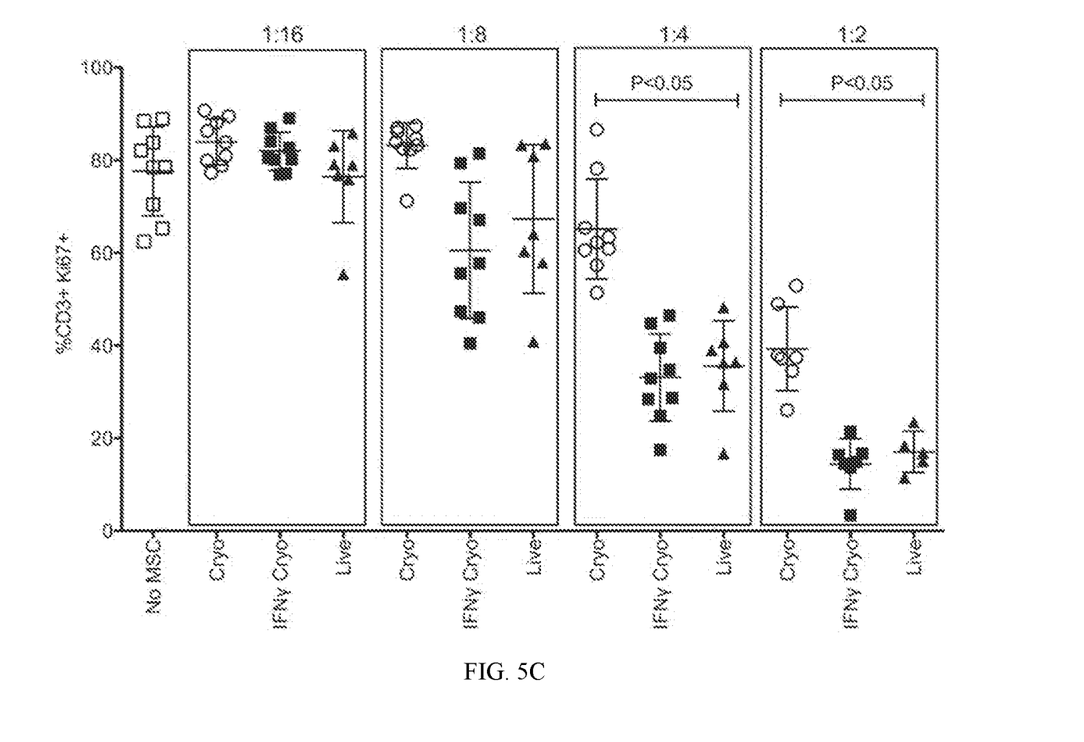
FIG. 5C shows data on the cumulative % of T cell proliferation (CD3 Ki67) with IFNgamma Cryo, Live MSC and PBMC ratio. Cumulative is plotted from multiple independent experiments tested with unique PBMC and MSC donors.
Figure 5D:
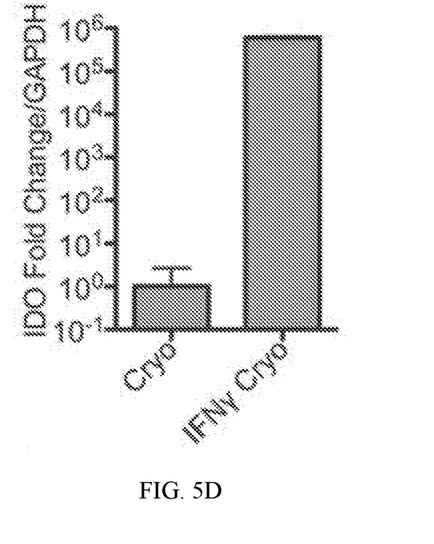
FIG. 5D shows data for IFNgamma licensed cryopreserved human MSCs that were thawed and RNA was extracted to quantitate the expression levels of IDO mRNA by quantitative sybr-green real time PCR. GAPDH mRNA levels were used as an internal control. Delta-delta CT method was applied to calculate the fold change.
Figure 5E:
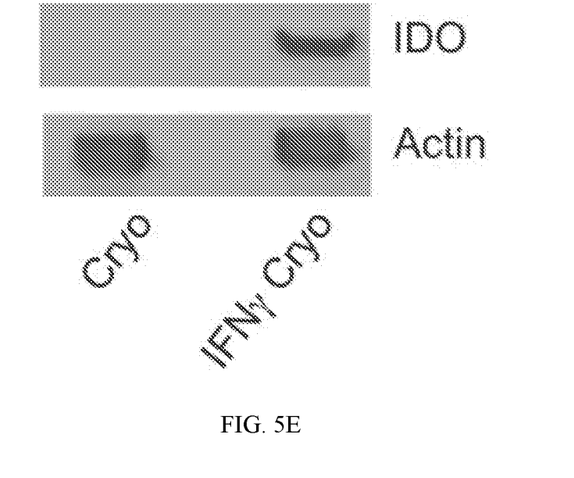
FIG. 5E shows a western blot analysis to show the IDO expression at protein levels in IFNgamma cryo MSCs. Actin was used as an internal control.
Figure 5F:
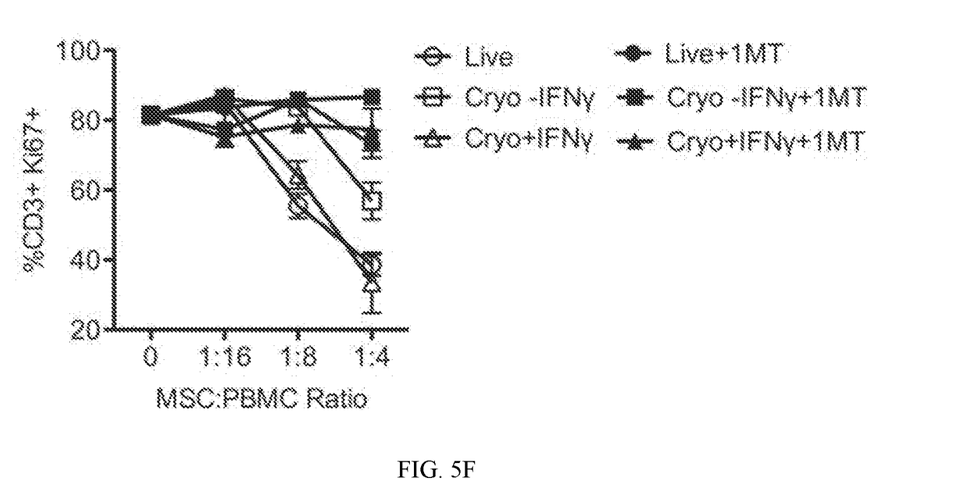
FIG. 5F shows data on live, cryo and IFNgamma cryo MSCs that were cocultured with activated PBMCs in the presence and absence of IDO blocker, 1-Methyl Tryptophan (1MT). Four days post, T cell proliferation was measured by flow cytometry.

IFNgamma but not Inhibitors of Autophagy and Caspase Pretreatment Prior to Cryopreservation Enhances Thawed Immunosuppressive Properties of Mesenchymal Stem Cells Whether pretreatment of mesenchymal stem cells with inhibitors of autophagy and caspase pathways, prior to cryopreservation would rescue frozen-thawed immunosuppressive properties of mesenchymal stem cells was tested. Frozen-thawed mesenchymal stem cells pretreated with Z-VAD-FMK (Pan caspase inhibitor) or 3-Methyl Adenine (autophagy inhibitor) prior to cryopreservation were defective in inhibiting T cell proliferation (FIG. 5A, 5B). IFNgamma enhances immunosuppressive properties of mesenchymal stem cells. Whether IFNgamma prelicensing prior to cryopreservation rescues thawed immunosuppressive properties of mesenchymal stem cells was investigated. IFNgamma prelicensed frozen-thawed mesenchymal stem cells (Hereafter called IFNgamma Cryo) inhibit T cell proliferation as well as actively growing Live MSCs (% CD3+Ki67+: No MSC (77±9), Live MSC (36±10), Cryo MSC (65±3) IFNgamma Cryo MSC (33±10)) (FIG. 5C). IFNgamma Cryo MSCs express IDO RNA and protein, which is preserved at thawing (FIG. 5D, 5E). Blocking of IDO catalytic activity with 1-Methyl Tryptophan (1MT) negates the suppressive effect of IFNgamma Cryo MSCs on T-cell proliferation (FIG. 5F) suggesting that intracellular IDO protein and its activity are preserved during freeze-thawing and play a significant role on IFNgamma Cryo immunosuppressive properties of mesenchymal stem cells.

Figure 6A:
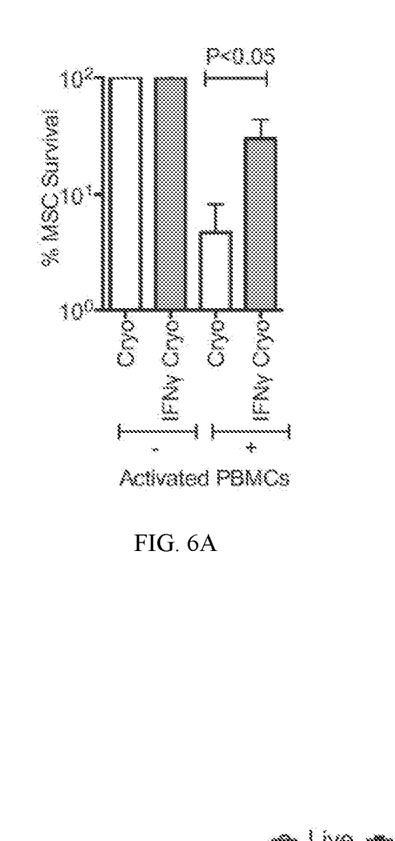
FIG. 6A shows data on the relative % survival of live, cryo and IFNgamma cryo MSCs cocultured with SEB activated PBMCs. CFSE labeled IFNgamma Cryo MSCs were cocultured with SEB activated PBMCs for 4 days in seeding ratio of 1:4. Trypsinized CFSE1 cells were counted in flow cytometry using counting bead normalization. IFNgamma Cryo MSC count in the absence of PBMCs were used for normalization and calculation of % survival of IFNgamma Cryo MSCs in the presence of PBMCs. IFNgamma prelicensing rescues frozen-thawed MSC's survival through inhibition of cytotoxic T cell degranulation.
Figure 6B:
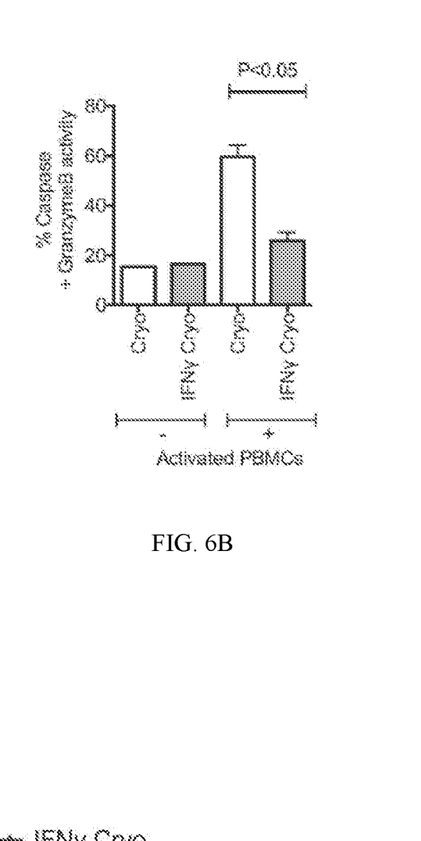
FIG. 6B shows percentage serine protease activity in cryo and IFNgamma cryo MSCs cocultured with SEB activated PBMCs.
Figure 6C:
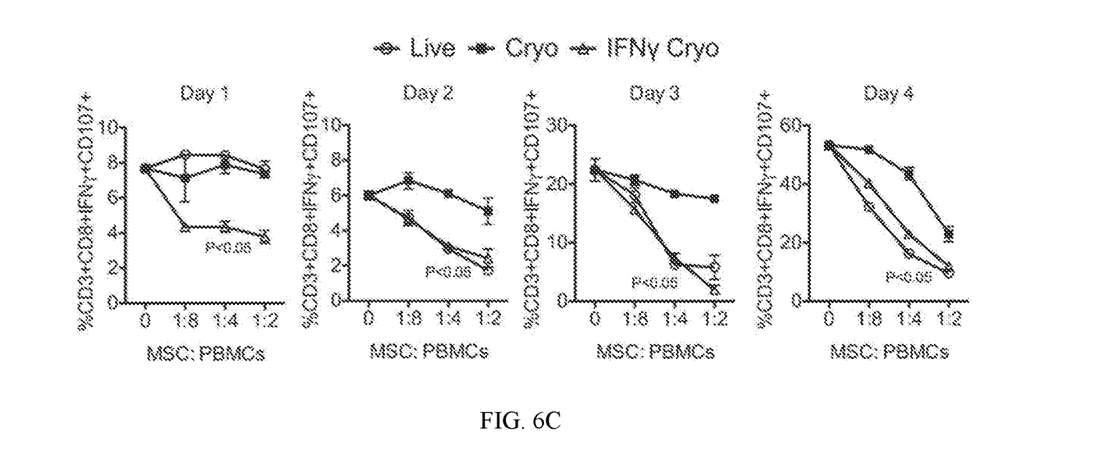

IFNgamma Prelicensing Prior to Cryopreservation Enhances Thawed Survival of Mesenchymal Stem Cells Through Inhibition of T Cell Degranulation To investigate the immunosuppressive mechanism of IFNgamma Cryo MSCs, the survival of ±IFNgamma Cryo MSCs cocultured with activated PBMCs were compared. IFNgamma prelicensing enhances frozen-thawed survival of mesenchymal stem cells following coculture with activated PBMCs (Cryo MSCs 5±2%, IFNgamma Cryo MSCs 30±7%) (FIG. 6A). Next, the effect IFNgamma of prelicensing on pro-cytotoxic serine protease activities of thawed mesenchymal stem cells was investigated. IFNgamma prelicensing attenuates serine protease activity on thawed mesenchymal stem cells upon coculture with activated PBMCs (Cryo MSCs 60±5%, IFNgamma Cryo MSCs 26±4%) (FIG. 6B). To further delineate IFNgamma dependent thawed resistance of mesenchymal stem cells to killing by activated T cells, the degranulation potential of cocultured T cells was analyzed. CD107a expression was utilized as a surrogate of perforin and granzyme B release by activated T cells. IFNgamma Cryo MSCs significantly inhibit the degranulation CD3+CD8+IFNgamma+T cells. Next, the kinetics of T cell degranulation in the presence and absence of live and ±IFNgamma Cryo mesenchymal stem cells was investigated. IFNgamma Cryo mesenchymal stem cells inhibit T cell degranulation at all the tested time points (FIG. 6C). However, Live and Cryo MSCs fail to inhibit T cell degranulation immediately at day 1, while live cells gain anti-degranulation properties in subsequent time points and Cryo MSCs display defective in all the tested time points (FIG. 6C). These results suggest that in contrast to thawed counterparts, live mesenchymal stem cells reactivated by IFNgamma acquire inhibitory properties to attenuate ongoing T cell degranulation.

Mesenchymal Stem Cell Isolation and Culture

Bone marrow aspirates were collected from iliac crest of consenting subjects enrolled in an IRB-approved study. Mononuclear cells were isolated from the bone marrow aspirates (1:2 diluted with Phosphate Buffer Saline) using Ficoll density gradient centrifuged at 400 g for 20 minutes. Collected mononuclear cells were plated in complete human MSC medium (α-MEM, 10% human platelet lysate (hPL), 100 U/ml penicillin/streptomycin/Amphotericin B) at 200,000 cell/cm$^2$. Non-adherent hematopoietic cells were removed by changing the medium after 3 days of culture and mesenchymal stem cells were allowed to expand for 7 days. Mesenchymal stem cells were passaged weekly and reseeded at 1,000 cells/cm$^2$. After the third passage, mesenchymal stem cell cultures were assayed by flow cytometric analysis for the absence of CD45+ and CD31+ contaminating cells and expression of CD44, CD73, CD90, and CD105. Assays were performed using mesenchymal stem cell between passage 2 and 6.

Mesenchymal Stem Cells Cryopreservation and Thawing

Mesenchymal stem cells at 70%-80% confluence were trypsinized and washed with complete medium. For IFN-gamma prelicensing, recombinant human IFNgamma was added at the concentration of 20 ng/ml in the MSC culture medium 48 hours prior to cryopreservation. Similarly, caspase inhibitor Z-VAD-FMK 50 uM or 3-Methyl Adenine 1 mM was used for the pretreatment of mesenchymal stem cells before cryopreservation. The cell pellet was resuspended with freezing media slowly at the concentration of 5-10×10$^6$ cells/ml. The following freezing media were tested: 5% Human Serum Albumin (HSA) in Plasmalyte/aMEM, 5%, 20%, 40%, 90% hPL in aMEM with 10% DMSO. For DMSO free animal protein free freezing media, CryoSOfree™ DMSO-free Cryopreservation Medium was used. According to manufacturer description, CryoSOfree™ is the animal protein free cryoprotectant containing polyampholytes with an appropriate ratio of amino and carboxyl groups (COOH to amine ration between 0.4 to 0.8). The cells were placed in the freezing container Nalgene® Mr. Frosty at the cooling rate of 1° C./minute. For step-down freezing, the following program was used in a CryoMed™ Controlled-Rate Freezer 1. Wait at 4.0° C.; 2. Ramp 1.0° C./minute until Sample=−6.0° C.; 3. Ramp 25.0° C./minute until Chamber=−50.0° C.; 4. Ramp 25.0° C./minute until Chamber=−14.0° C.; 5. Ramp 1.0° C./minute until Chamber=−45.0°; 6. Ramp 10.0° C./minute until Chamber=−90.0° C.; 7. Hold −90.0° C. for 5.0 minutes. The cells were then transferred in to liquid nitrogen. For thawing, the cells were kept at 37° C. water bath for one minute and immediately transferred in to MSC complete medium for centrifugation two times. Viable cell count is then determined by mixing equal volumes of 0.4% Trypan blue and Cell mixture and analyzed either using a hemacytometer or by automated cell counting. A secondary measure of viability of MSCs cultures was monitored by FACS analysis using 7-aminoactinomycin D (7-AAD) and analyzed through FACScanto II cytometer (BD, U.S.). Prestoblue dye reduction assay was performed according to manufacturer instructions. Briefly MSCs and PrestoBlue® Cell Viability Reagent were incubated for three hours and absorbance were read at 570 nm and 600 nm wavelengths.

Mesenchymal Stem Cells and T Cell Coculture

Live or thawed mesenchymal stem cells and PBMCs were cocultured at the indicated ratio in 96 well plates. PBMCs were prepared from healthy individuals by Ficoll density gradient were resuspended in RPMI-1640 complete medium (10% heat inactivated serum, 100 U/ml penicillin/streptomycin, L-glutamine, 10 mM HEPES). PBMCs were activated with 500 ng/ml Staphylococcal enterotoxin B (SEB) or 2 ul dynabeads. For IDO blocking 1-methyl-DL-tryptophan (1 mM concentration) were added to the coculture. For non-contact MSC and PBMC culture, mesenchymal stem cells and SEB/bead activated PBMCs were cultured in the bottom and transwell respectively using Corning® Costar® 0.4 uM Transwell® cell culture inserts. For Ki67 Proliferation assay, cells were incubated for 4 days and were subjected to intracellular Ki67 staining according to manufacturer instructions. Degranulation assay was performed with CD107 antibody staining during stimulation at the indicated time points for 12 hours with monensin and brefeldin A. Intracellular flow cytometry staining was performed with of BD Cytofix and Cytoperm procedures according to the manufacturer instructions and with the antibodies APCCy7-antiCD3, PerCP-antiCD8 and APC-IFNgamma.

The invention claimed is:

1. A method of cryopreserving mesenchymal stem cells comprising
   mixing mesenchymal stem cells with interferon gamma at a concentration of 20 ng/mL in culture medium for 48 hours providing mixed mesenchymal stem cells, and cooling the mixed mesenchymal stem cells to a temperature below zero degrees Celsius providing frozen interferon gamma exposed mesenchymal stem cells, wherein mixing is prior to cooling the mixed mesenchymal stem cells, and
   thawing the frozen interferon gamma exposed mesenchymal stem cells to a temperature above zero degrees Celsius providing thawed interferon gamma exposed mesenchymal stem cells that express indoleamine 2,3-dioxygenase (IDO) mRNA with greater than a 100-fold change in concentration when compared to cryopreserved mesenchymal stem cells that were not mixed with interferon gamma prior to freezing.

2. The method of claim 1, wherein the temperature is less than negative 50 degrees Celsius.

3. The method of claim 1, wherein the mesenchymal stem cells are in a cryoprotectant during cooling.

4. The method of claim 3 wherein the cryoprotectant comprises a component selected from monosaccharide, a disaccharide, trehalose, glycerol, ethylene glycol, and propylene glycol, or combinations thereof.

5. The method of claim 3 wherein the cryoprotectant comprises a polyampholyte.

6. The method of claim 1 further comprising mixing the thawed interferon gamma exposed mesenchymal stem cells with a component selected from interferon-gamma, interleukin-1beta, interleukin-1alpha, transforming growth factor-beta, interleukin-6, interleukin-10, prostaglandin-E2, hepatocyte growth factor, tumor necrosis factor-alpha, or combinations thereof.

7. The method of claim 1 further comprising mixing the thawed interferon gamma exposed mesenchymal stem cells with interferon-gamma optionally in combination with a cytokine selected from interleukin-1beta, interleukin-1 alpha, and tumor necrosis factor-alpha.

8. The method of claim 1 further comprising purifying, plating, passaging, and harvesting the thawed mesenchymal stem cells providing regenerated mesenchymal stem cells.

* * * * *